(12) United States Patent
Hissoiny et al.

(10) Patent No.: US 10,668,300 B2
(45) Date of Patent: Jun. 2, 2020

(54) RADIATION TREATMENT PLANNING OR ADMINISTRATION ELECTRON MODELING

(71) Applicant: Elekta, Inc., Atlanta, GA (US)

(72) Inventors: Sami Hissoiny, Longueuil (CA); Michel Moreau, Verona, WI (US)

(73) Assignee: Elekta, Inc., Atlanta, GA (US)

( * ) Notice: Subject to any disclaimer, the term of this patent is extended or adjusted under 35 U.S.C. 154(b) by 356 days.

(21) Appl. No.: 15/836,474

(22) Filed: Dec. 8, 2017

(65) Prior Publication Data

US 2019/0175940 A1  Jun. 13, 2019

(51) Int. Cl.
G06G 7/56 (2006.01)
A61N 5/10 (2006.01)

(52) U.S. Cl.
CPC ......... *A61N 5/1031* (2013.01); *A61N 5/1039* (2013.01); *A61N 5/1064* (2013.01); *A61N 5/1037* (2013.01); *A61N 5/1038* (2013.01); *A61N 2005/1034* (2013.01); *A61N 2005/1052* (2013.01); *A61N 2005/1055* (2013.01); *A61N 2005/1058* (2013.01); *A61N 2005/1061* (2013.01)

(58) Field of Classification Search
CPC ... A61N 5/1031; A61N 5/1039; A61N 5/1064
USPC .......................................................... 703/5
See application file for complete search history.

(56) References Cited

U.S. PATENT DOCUMENTS

| 2005/0197564 A1* | 9/2005 | Dempsey | G01R 33/381 600/411 |
| 2008/0091388 A1* | 4/2008 | Failla | A61N 5/1031 703/2 |
| 2014/0330108 A1* | 11/2014 | Dempsey | A61B 90/37 600/411 |

FOREIGN PATENT DOCUMENTS

WO  2019113228  6/2019

OTHER PUBLICATIONS

"International Application Serial No. PCT/US2018/064095, International Search Report dated Mar. 28, 2019", 4 pgs.
"International Application Serial No. PCT/US2018/064095, Written Opinion dated Mar. 28, 2019", 6 pgs.
Kawrakow, I., et al., "The EGSnrc Code System: Monte Carlo Simulation of Electron and Photon Transport", NRCC Report PIRS-701, © NRC Canada, 2001-2015, (Jun. 9, 2017), 323 pgs.

* cited by examiner

*Primary Examiner* — Andre Pierre Louis
(74) *Attorney, Agent, or Firm* — Schwegman Lundberg & Woessner, P.A.; Sanjay Agrawal

(57) ABSTRACT

Radiation treatment planning and administration can include a Monte Carlo computer simulation tool to simulate photo-generated electrons in tissue. In the simulation, electrons that have left tissue voxels and entered air voxels can be evaluated to identify electrons that are circling along a spiraling trajectory in the air voxels. After at least one full spiraling circumference or other specified distance has been traversed using a detailed electron transport model, a simpler linear ballistic motion model can be instituted. This speeds simulation while accurately accounting for spiraling electrons that re-enter tissue voxels.

22 Claims, 6 Drawing Sheets

RADIATION TREATMENT PLANNING OR ADMINISTRATION ELECTRON MODELING

TECHNICAL FIELD

This document pertains generally, but not by way of limitation, to planning or administration of radiation treatment such as to a human or animal subject.

BACKGROUND

Radiation therapy can involve administering a dose of radiation to a human or animal subject. Careful planning can help ensure that the radiation reaches a target region of interest, while avoiding one or more nearby regions that are not expected to benefit from radiation and that may be impacted by side-effects of such radiation.

Three-dimensional (3D) imaging data can be used to plan radiation treatment. Such 3D imaging data can be obtained, for example, from a magnetic resonance (MR) or computed tomography (CT) imaging device. The 3D imaging data can include voxels representing imaging data of various densities. For example, 3D voxel data of tissue within the subject will represent a higher density than voxels representing air outside of the subject. Voxels corresponding to air within a body cavity (e.g., within the bronchial tubes, for example, will also exhibit less density than surrounding tissue. Bone tissue voxels will have a higher density than softer tissue voxels.

One technique for delivering radiation to a desired region of interest within a subject can involve generating photons. For example, photons incident into tissue can generate free electrons within the tissue. Free electrons can follow a complex trajectory within the tissue, particularly under the influence of a magnetic field, such as can be present when radiation therapy is administered when the subject is within the magnetic field of an MR imaging device.

SUMMARY

An applied magnetic field can result in a spiraling trajectory for an electron in a vacuum, and can be subject to more complex interactions, including energy loss, within tissue regions of the subject. Similar to the electron trajectory in a vacuum, an electron trajectory through air will follow a generally spiraling trajectory within an applied magnetic field, subject to some energy losses from interaction with the air.

Electron transport can be computer-simulated, such as using a Monte Carlo simulation, such as for radiation treatment planning. For example, a Condensed History technique of simulating electron transport is described in I. Kawrakow et al., "The EGSnrc Code System: Monte Carlo Simulation of Electron and Photon Transport, Ionizing Radiation Standards, National Research Council Canada, Ottawa, Canada (NCRCC Report PIRS-701), Jun. 9, 2017 (See, e.g., Section 2.4, entitled Simulation of Electron Transport.)

Such Monte Carlo computer simulation of electron-transport can be computationally very complex and, therefore, time-consuming. Accurate computer simulation of the radiation dose—accounting for electron transport through tissue and air (or through media of various mass densities and Z-equivalent values) in the presence of an applied magnetic field and its resulting Lorentz force on the electron's trajectory—is needed for computing a spatially modeled radiation dose including using voxel density information obtained from 3D imaging data. The present inventors have recognized, among other things, a need for reducing the computation time involved for computing a spatially modeled radiation dose, while maintaining sufficient accuracy such as to avoid a systematic underdose or overdose of radiation to the region of interest, and with sufficient selectivity to avoid delivering an unnecessary radiation dose outside the region of interest.

As an illustrative example, the present inventors have recognized that it can be useful to model an electron generated within the subject's tissue that leaves the tissue and re-enters the tissue due to the spiraling trajectory imposed by the Lorentz force of an applied magnetic field. While the complex Condensed History technique can be used to model the spiraling trajectory of an electron exiting tissue, after the electron has traversed a cumulative path length of at least one spiraling circumference without re-entry into tissue, a more simplified linear ballistic motion modeling can be applied—which can help speed the Monte Carlo simulation considerably, as explained further herein. More generally, this technique can be applied to an electron leaving a more dense voxel to enter a region of one or more less dense voxels (e.g., voxels having a density below a certain user-defined density threshold) in the presence of an applied magnetic field, such that it can be applied to entering an air cavity within the subject, not just to entering surrounding air outside of the subject.

Optionally, the initial location of the transition from the more complex Condensed History model to the more simplified linear ballistic motion modeling for the Monte Carlo simulation can be randomly or pseudo-randomly assigned along the spiraling trajectory, such as to avoid systematic bias being imposed by this technique by assigning the same transition location to each electron.

Furthermore, energy loss due to travel through air can be properly accounted for, even while the spiraling electron trajectory is being approximated as linear ballistic motion, as explained herein.

For example, this document describes a technique that can include a machine-implemented method of modeling a dose of radiation in a subject in an applied magnetic field. A portion of the modeled dose can include a return electron effect from electrons leaving and returning to a region due to a spiraling trajectory induced by the applied magnetic field. The technique can include receiving image data segmented into higher density voxels and lower density voxels. A cumulative path length can be calculated, such as for an electron leaving a higher density voxel and entering a lower density voxel. This cumulative path length can be set to zero when the electron returns from a lower density voxel to a higher density voxel. When the cumulative path length exceeds a specified path length threshold in one or more contiguous lower density voxels in the applied magnetic field, the trajectory of the electron in the one or more contiguous lower density voxels can be modeled as a linear ballistic motion, such as in a direction that can be aligned with the applied magnetic field. In an example, when the cumulative path length does not exceed the specified path length threshold in the one or more contiguous lower density voxels in the applied magnetic field, the electron trajectory can be modeled using a more complex electron transport model (e.g., Condensed History or another more complex electron transport model) providing a spiraling trajectory induced by the applied magnetic field in the one or more contiguous lower density voxels. In an example, the more complex model can also be used within regions represented by the higher density voxels, such as within the subject's tissue.

The above is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, techniques that can help improve the speed of Monte-Carlo simulation of a radiation dose, such as for radiation treatment planning or administration, particularly in an environment in which an applied magnetic field is present, such as with an MR imaging device. In particular, electrons in or near the subject can be modeled using a complex spiraling trajectory, where appropriate, but the modeling can be simplified to a more computationally efficient linear ballistic motion trajectory model, when appropriate, such as explained further herein. For example, free electrons may be generated within the subject, such as within tissue. In a particular illustrative example, such free electrons may result from incident photons provided by a radiation therapy device. Regardless of how generated, such free electrons in or near the subject can be subject to a Lorentz force resulting from the applied magnetic field, which can be modeled by a spiraling trajectory, or by a more computationally efficient linear ballistic motion trajectory, as explained herein.

Figure 1:
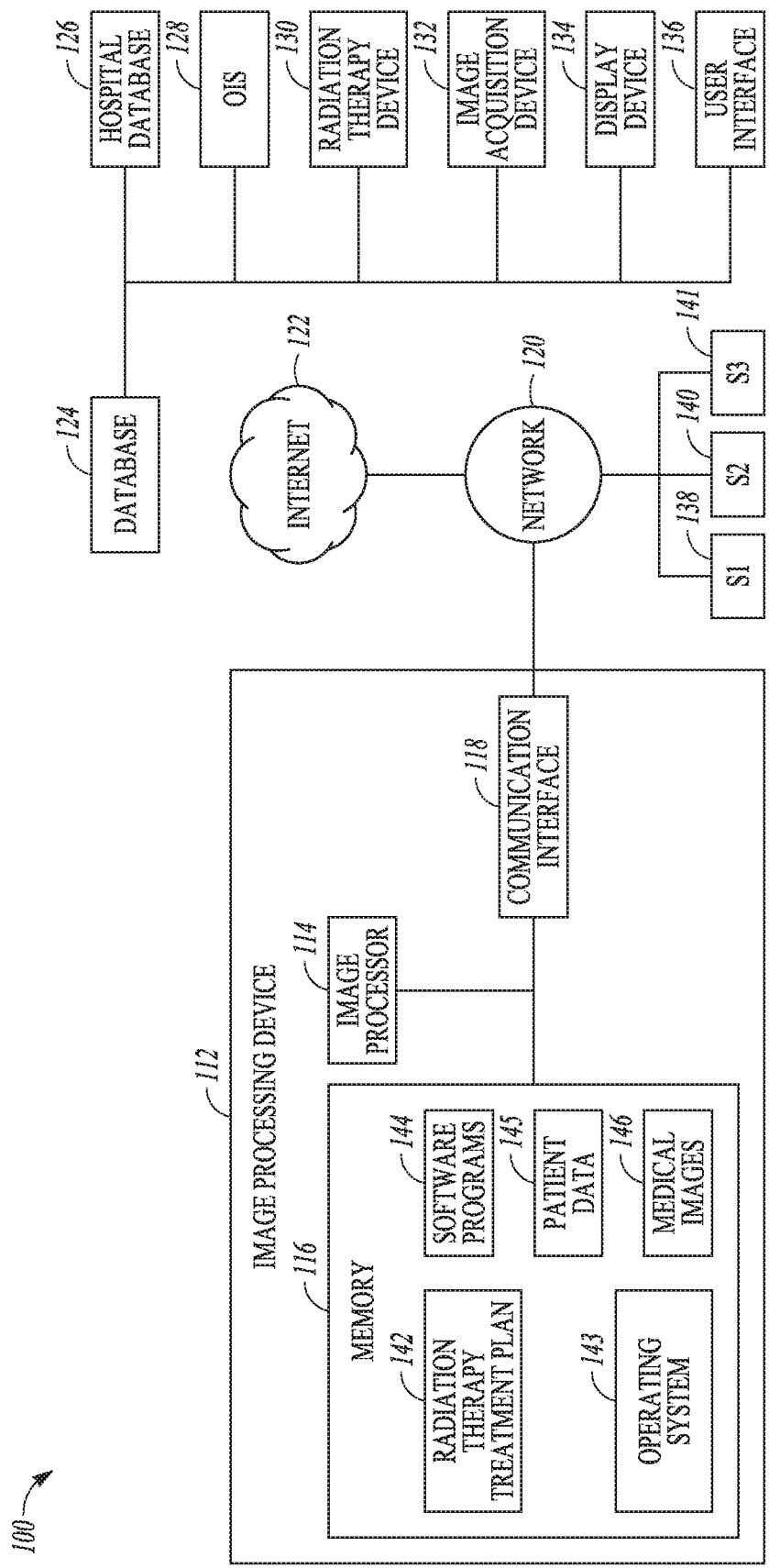
FIG. 1 illustrates an example of a radiotherapy system.

FIG. 1 illustrates an exemplary radiotherapy system 100 for providing radiation therapy to a patient, to a portion of a patient, or to a "phantom", which can include a target object representing the patient or the portion of the patient. The radiotherapy system 100 includes an image processing device, 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114 and a communication interface 118. The memory device 116 may store computer-executable instructions, such as an operating system 143, a radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114. In one embodiment, the software programs 144 may convert medical images of one format (e.g., MRI) to another format (e.g., CT) by producing synthetic images, such as a pseudo-CT image. For instance, the software programs 144 may include image processing programs to train a predictive model for converting a medial image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target, or any other structural aspect useful to neural network learning. The memory device 116 may store data, including medical images 146, patient data 145, and other data required to create and implement a radiation therapy treatment plan 142.

In addition to the memory 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software 144 when executed may train a boundary detector, or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 114 can execute sequences of computer program instructions, stored in memory 116, to perform various operations, processes, methods that will be explained in greater detail below.

The memory device 116 can store medical images 146. In some embodiments, the medical images 146 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 146 may be received and stored in any type of data or any type of format that the image processing device 112 may use to perform operations consistent with the disclosed embodiments. The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory 116. The Communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtain CT images (e.g., medical images 146). In addition, network 120 may be connected to internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data that is information associated with a radiation therapy device 130, image acquisition device 132, or other machines relevant to radiotherapy. Machine data information may include radiation beam size, arc placement, beam on and off time duration, machine parameters, segments, multi-leaf collimator (MLC) configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 114 may communicate with database 124 to read images into memory 116 or store images from memory 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 124 received from image acquisition device 132. Database 124 may store data to be used by the image processor 114 when executing software program 144, or when creating radiation therapy treatment plans 142. Database 124 may store the data produced by the trained neural network including the network parameters constituting the model learned by the network and the resulting predicted data. The image processing device 112 may receive the imaging data 146 (e.g., 2D MRI slice images, CT images, 2D Fluoroscopy images, X-ray images, 3DMRI images, 4D MRI images, etc.) either from the database 124, the radiation therapy device 130 (e.g., a MRI-Linac), and/or the image acquisition device 132 to generate a treatment plan 142.

In an embodiment, the radiotherapy system 100 can include an image acquisition device 132 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 132 can be stored within database 124 as either imaging data and/or test data. By way of example, the images acquired by the imaging acquisition device 132 can be also stored by the image processing device 112, as medical image data 146 in memory 116.

In an embodiment, for example, the image acquisition device 132 may be integrated with the radiation therapy device 130 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "near real-time" while a patient is undergoing radiation therapy treatment, for example, when using the radiation therapy device 130. "Near real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as beam angles, dose-histogram-volume information, the number of radiation beams to be used during therapy, the dose per beam, and the like.

The image processor 114 may generate the radiation therapy treatment plan 142 by using software programs 144 such as treatment planning software, such as Monaco®, manufactured by Elekta AB of Stockholm, Sweden. In order to generate the radiation therapy treatment plans 142, the image processor 114 may communicate with the image acquisition device 132 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer, e.g., Apple iPad®, Lenovo Thinkpad®, Samsung Galaxy®, etc.

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, the image acquisition device 132 could be implemented as a virtual machine. Given the processing power, memory, and computational capability available, the entire radiotherapy system 100 could be implemented as a virtual machine.

FIG. 2A illustrates an exemplary radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

Figure 2:
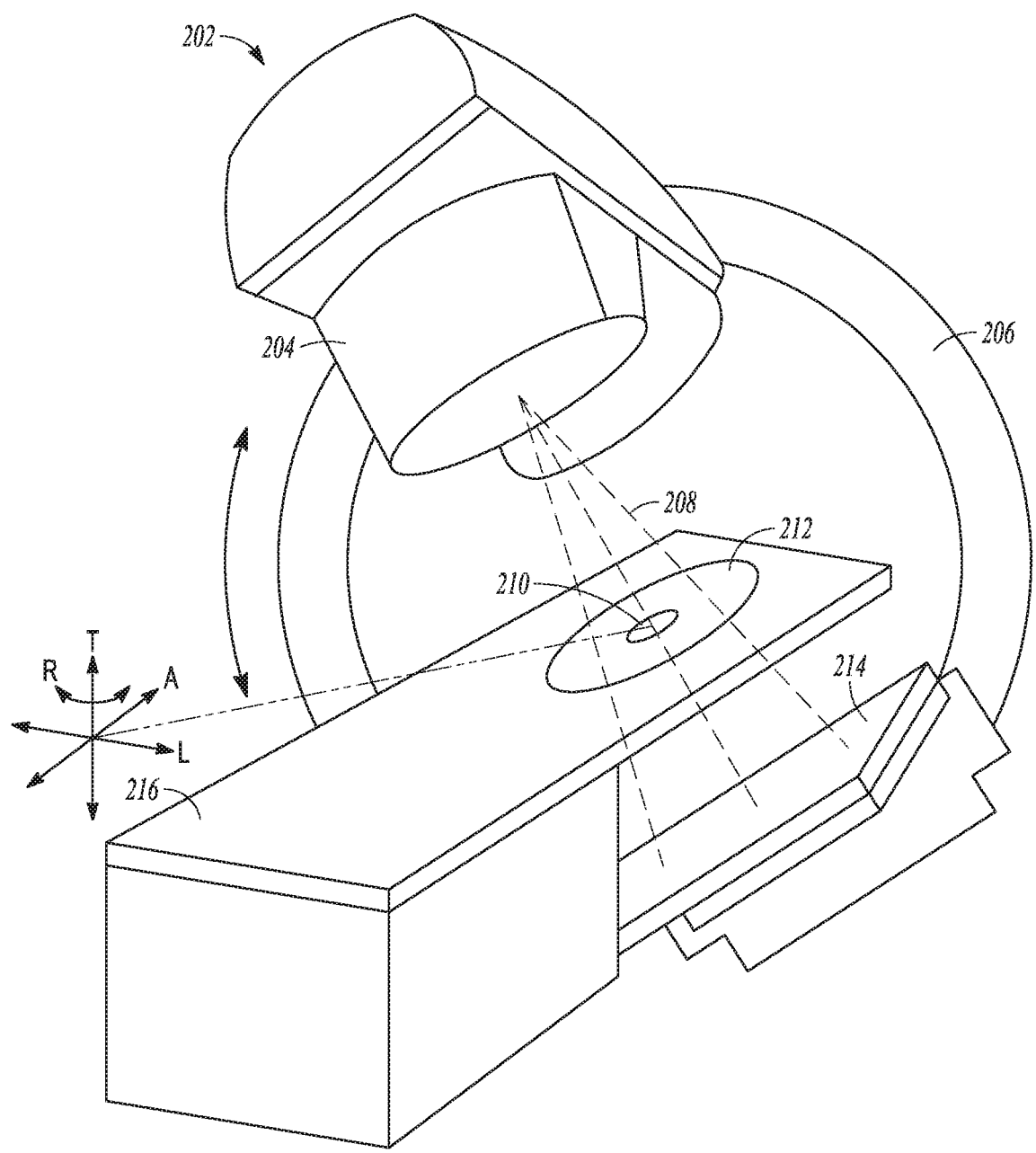
FIG. 2 illustrates an example of a radiation therapy system that can include radiation therapy output configured to provide a therapy beam.

In FIG. 2, a patient can be positioned in a region 212, supported by the treatment couch 216 to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

FIG. 2 illustrates generally illustrate an embodiment of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

In another embodiment, a radiation therapy device can be a combination of a linear accelerator and an image acquisition device. In some embodiments, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Techniques to Model Radiation Dose to Subject in Applied Magnetic Field

The present inventors have recognized, among other things, a need to help improve the speed of Monte-Carlo simulation of a radiation dose, such as for radiation treatment planning or administration, particularly in an environment in which an applied magnetic field is present, such as within an MR imaging device. For example, certain MR imaging devices provide a 1.5 T magnetic field, while others provide a magnetic field of 0.5 T, 0.35 T, or 0.2 T. The present techniques can also be useful at other levels of magnetic field.

In particular, electrons in or near the subject can be modeled using a complex spiraling trajectory, where appropriate, but the modeling can be simplified to a more computationally efficient linear ballistic motion trajectory model, when appropriate, such as explained further herein. For example, free electrons may be generated within the subject, such as within tissue. In a particular illustrative example, such free electrons may result from incident photons provided by a radiation therapy device. Regardless of how generated, such free electrons in or near the subject can be subject to a Lorentz force resulting from the applied magnetic field, which can be modeled by a spiraling trajectory, or by a more computationally efficient linear ballistic motion trajectory, as explained herein.

This can help improve the speed of Monte-Carlo simulation of a radiation dose, such as for radiation treatment planning or administration. Such techniques can also be applied to electrons or photons originating from a titanium or other implant within the subject, or from a brachytherapy seed or other radiative source located upon or within the subject who, in turn, is located within an applied magnetic field.

Figure 3C:
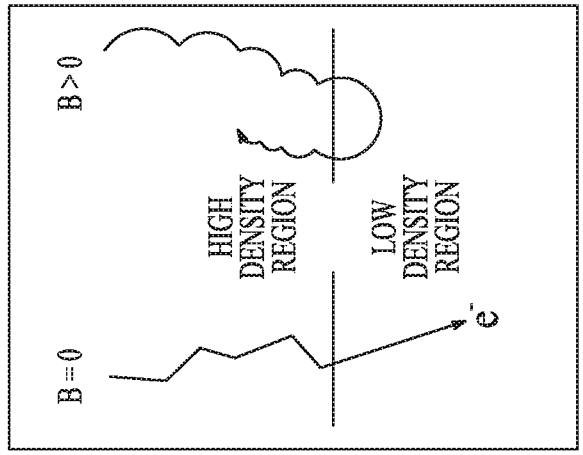
FIG. 3C illustrates conceptually an interesting case in which the electrons are leaving a higher density region to enter a lower density region.
Figure 3B:
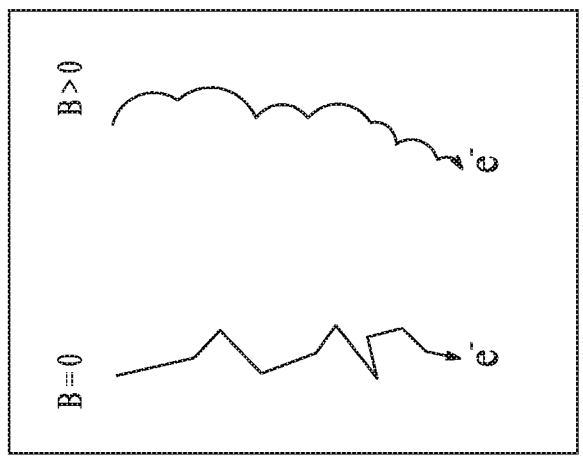
FIG. 3B illustrates conceptually an example of electron trajectories through tissue of a human or animal subject, on in the absence of an applied magnetic field (B=0, shown at left), and in the presence of an applied magnetic field (B>0, shown on right).
Figure 3A:
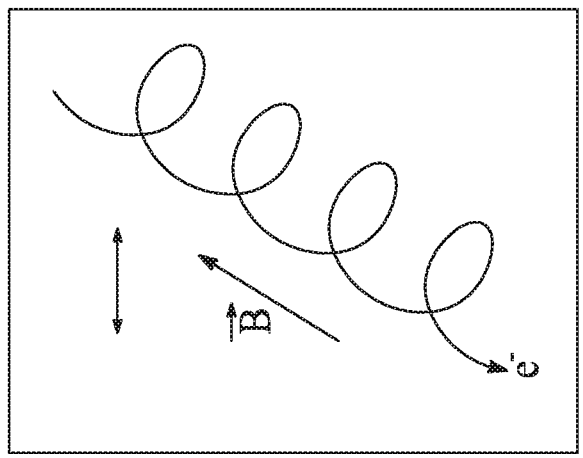
FIG. 3A illustrates conceptually an example of a trajectory of an electron in a vacuum under an applied magnetic field having a magnitude B>0.

FIG. 3A illustrates conceptually an example of a trajectory of an electron in a vacuum under an applied magnetic field B having a magnitude B>0. The electron will follow a spiraling trajectory, creating a helical path, as shown. The electron trajectory in air under a similar magnetic field B will follow a similar spiraling trajectory, creating a similar helical path, but the electron will experience some energy loss as a function of its cumulative path traveled through the air.

FIG. 3B illustrates conceptually an example of electron trajectories through tissue of a human or animal subject, in the absence of an applied magnetic field (B=0, shown at left), and in the presence of an applied magnetic field (B>0, shown on right). Interactions with tissue will alter that path of an otherwise generally linear trajectory in the absence of an applied magnetic field, shown at left in FIG. 3B, and will also alter a path of an otherwise generally spiraling helical trajectory, shown on the right of FIG. 3B.

FIG. 3C illustrates conceptually an interesting case in which the electrons are leaving a higher density region to enter a lower density region. An example of such a case is an electron exiting tissue of the subject and entering an air region around the subject—or even entering an air region within the subject, such as by the electron entering into an air passage such as a trachea. In the absence of an applied magnetic field (B=0, shown at left of FIG. 3C), upon entering the lower density air region, the electron can take a generally linear trajectory oriented in a direction that can be influenced by the structure of the tissue that the electron is leaving. In the presence of a magnetic field (B>0, shown at right of FIG. 3C), upon entering the lower density air region, the electron can commence a spiraling trajectory beginning in an orientation that can be influenced by the structure of the tissue that the electron is leaving. As shown at right in FIG. 3C, in the presence of the magnetic field, there is a chance that an electron's spiraling trajectory can bring it back to re-enter the tissue. This can be referred to as an electron return effect (ERE). In such a case, the re-entering electron can further contribute to the radiation dose received by the tissue of the subject. Therefore, modeling and simulating such electron tissue re-entry events can be important to provide an accurate simulation of radiation dose, such as for use in radiation treatment planning or administration. On the other hand, expending computational resources during Monte Carlo computer simulation to continue to accurately model electrons that have left the subject and are on a trajectory never to return can be time-consuming and computationally expensive, without yielding any benefit. Such drawbacks can impede the ability to run multiple simulations of different treatment plan scenarios to evaluate and choose from.

Figure 4:
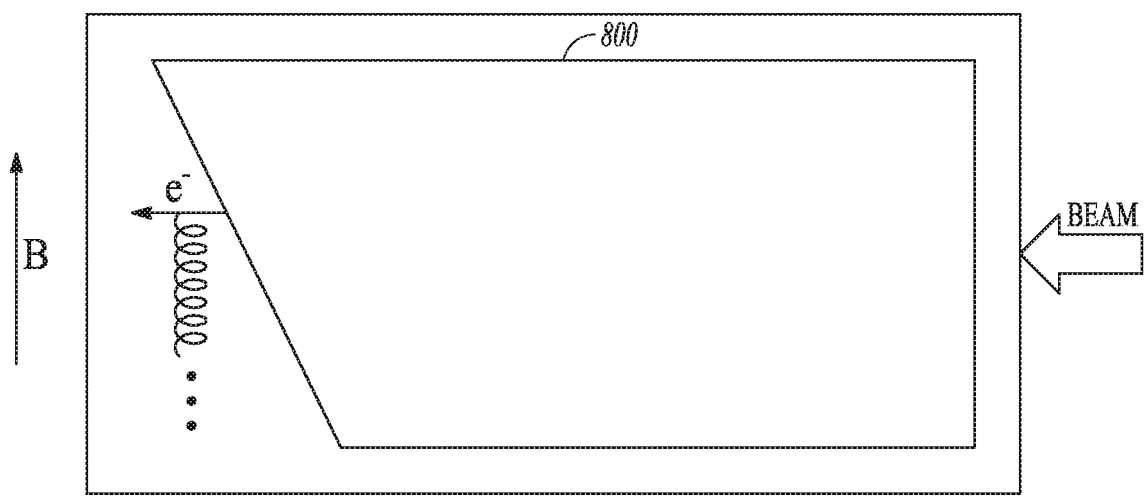
FIG. 4 illustrates conceptually a region of tissue within a subject targeted by an incident photon beam ("beam"), wherein the region of tissue of the subject is present within a magnetic field "B" in the direction shown in FIG. 4.

FIG. 4 illustrates conceptually a region of tissue within a subject targeted by an incident photon beam ("beam"), wherein the region of tissue 800 of the subject is present within a magnetic field "B" in the direction shown in FIG. 4. Incident photons can interact with tissue and free electrons (which can be referred to as "generated" electrons) within the tissue 800 of the subject. Within the tissue 800 with the magnetic field B present, the electrons can follow trajectories such as illustrated in the right hand side of FIG. 3B. FIG. 4 illustrates an example of an electron, e−, leaving the tissue 800 at an angle that is not perpendicular to the tissue-air interface boundary, with a trajectory of the departing electron, e−, being in a lateral direction to the magnetic field, B. As illustrated conceptually in FIG. 4, the magnetic field B can cause the laterally-departing electron, e−, to assume a spiraling trajectory in a direction that is aligned with the magnetic field B. Unless this departing electron, e−, re-enters the tissue 800, such as is most likely to occur during the first spiraling circumference in air, it is wasteful to continue to expend computational resources to accurately model the spiraling path of this electron, e−, in the Monte Carlo computer simulation. Instead, the trajectory of this electron, e−, can be more efficiently represented as linear ballistic motion in a direction that is aligned to the B field. Energy losses incurred by this electron, e−, due to interactions with air molecules can also be adequately and more efficiently modeled using the linear ballistic motion model, such as in the Monte Carlo computer simulation. If the linear ballistic motion results in the electron, e−, re-entering the tissue 800, more complex spiraling motion modeling can then be resumed in the Monte Carlo computer simulation.

Figure 5:
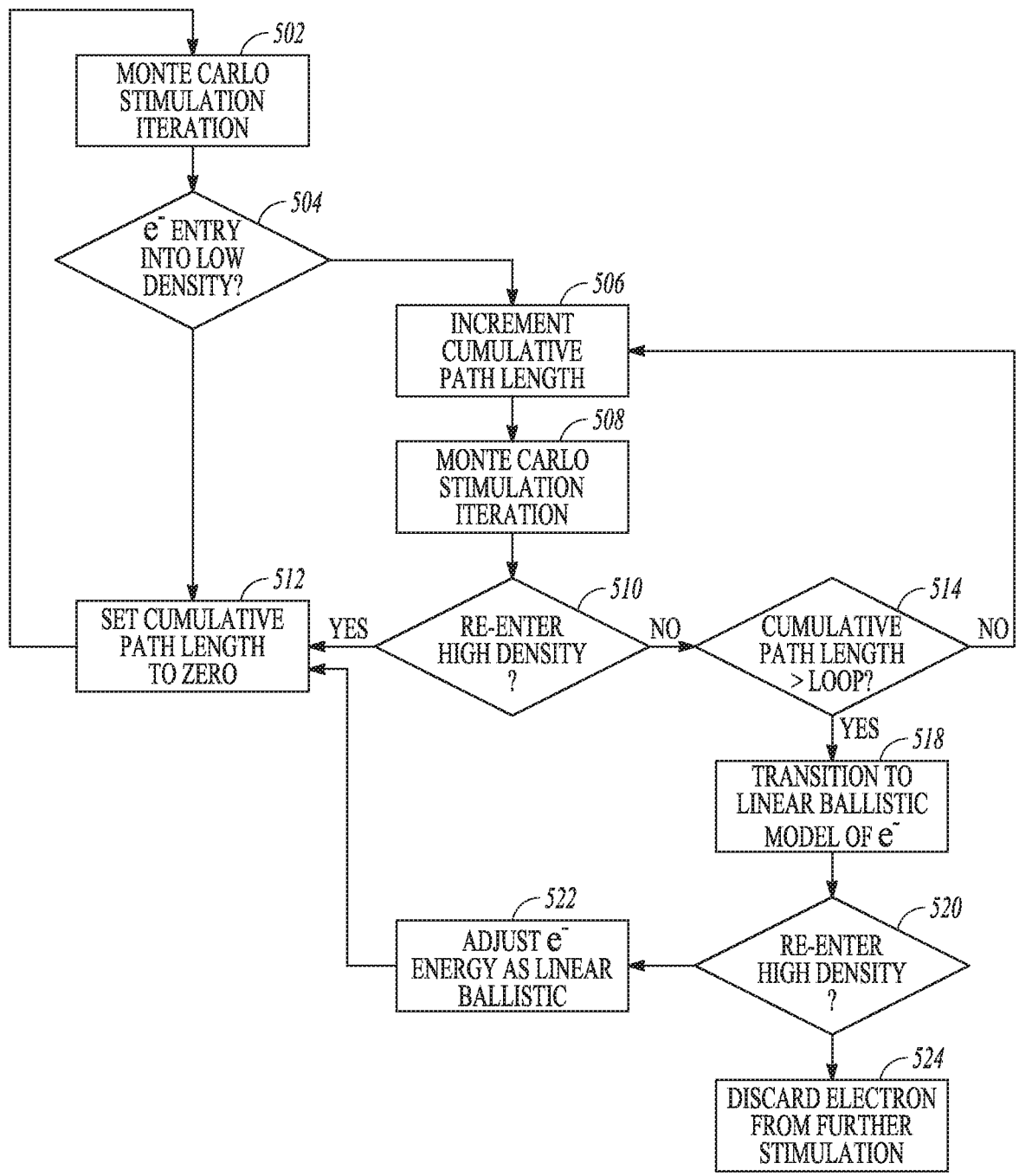
FIG. 5 illustrates an example of portions of a method, such as can be performed by a computer processor circuit, of a computer simulation that can include modeling a dose of radiation in a subject, such as where a portion of the subject can be located within an applied magnetic field, such as within the magnetic field produced by a magnetic resonance (MR) imaging device.

FIG. 5 illustrates an example of portions of a method 500, such as can be performed by a computer processor circuit, of a computer simulation that can include modeling a dose of radiation in a subject, such as where a portion of the subject can be located within an applied magnetic field, such as within the magnetic field produced by a magnetic resonance (MR) imaging device. As explained herein, the computer simulation technique can account for a return electron effect from electrons computer-simulated as leaving and returning to a region due to a spiraling trajectory induced by the computer-simulated Lorentz force of the computer-simulated applied magnetic field.

At 502, a Monte Carlo simulation iteration can be performed, such as using three-dimensional (3D) imaging data about a portion of the subject. The imaging data can include a spatial 3D arrangement of voxels. Each voxel can include an indication of the corresponding density of tissue observed by the MR or other imaging device. For example, regions of bone within the subject will be represented by a higher density value than a region of softer tissue, which, in turn, will be represented by a higher density value than an air region within or outside of the subject. In an example, the imaging data can be segmented into higher density values and lower density voxels, such as by comparing the voxel density value to a threshold value to categorize between the two, such as to differentiate between within-patient voxels, and outside-of-patient voxels, or to differentiate between within-patient tissue voxels and "air" voxels that can be located either outside-of-patient voxels, or within the patient in air regions.

At 502, the Monte Carlo computer simulation can include simulation of photons generated by a radiation therapy device incident onto a tissue region of the subject as represented within the 3D imaging data. The Monte Carlo simulation at 502 can also model resulting electrons generated within the tissue, such as by the incident photons or otherwise. For each such resulting electron, an associated cumulative path length datum can be set to zero when any iteration of the detailed Monte Carlo simulation at 502 indicates that such electron is within a high-density voxel, such as within a tissue voxel.

The Monte Carlo simulation can model the trajectory of such generated electrons within the high-density voxels, such as tissue voxels, using a "detailed electron transport model" including the simulated Lorentz force on electron transport within a simulated applied magnetic field, such as explained above with respect to FIGS. 3B and 3C. The Monte Carlo simulation at 502 can include using a Condensed History technique or similar simulation, which can include a detailed electron transport simulation model of electron transport, such as described in I. Kawrakow et al., "The EGSnrc Code System: Monte Carlo Simulation of Electron and Photon Transport, Ionizing Radiation Standards, National Research Council Canada, Ottawa, Canada (NCRCC Report PIRS-701), Jun. 9, 2017 (See, e.g., Section 2.4, entitled Simulation of Electron Transport.) The "detailed electron transport simulation model" will yield a spiraling trajectory for an electron in air due to the Lorentz force within the simulated applied magnetic field. The detailed electron transport model can be applied to electrons within high density voxels, and can also be applied in a more limited fashion within low density voxels, until transition to a more computationally efficient linear ballistic motion model can occur, as explained herein, while still allowing the "detailed electron transport simulation model" to simulate a trajectory curvature that can account for the return electron effect, as explained herein.

At 504, if an iteration of the detailed Monte Carlo simulation at 502 models transport of the electron out of a high-density region (e.g., from a tissue voxel region) into a lower-density region (e.g., into air voxel region within or outside the subject), then such an electron departing tissue and entering air can be monitored for possible simplified simulation using a more computationally efficient linear ballistic model, rather than the more complex detailed electron transport model capable of accounting for spiraling-type motion induced by the Lorentz force in an applied magnetic field, such as beginning with a sequence of acts indicated by 506. Otherwise, process flow can continue to 512 to set or reset to zero an electron cumulative path length datum corresponding to individual electrons being simulated, and can then return to 902 to continue the next Monte Carlo simulation iteration of any such electrons. It should be noted that monitoring of one or more simulated electrons leaving tissue and entering air is carried out in parallel and in conjunction with the Monte Carlo simulation iterations at 502 of other electrons that remain within a tissue voxel region.

At 506, for a given electron departing tissue and entering air, a cumulative path length datum for that electron can initially be set to zero upon entry into air. The cumulative path length datum can be used to make the decision as to whether that electron should be simulated using the more detailed electron transport model as having undergone one full spiraling circumference in air (or other specified cumulative path length datum threshold value), after which, such an electron in an air-region can be switched from the more computationally intensive detailed electron transport model (which can account for spiraling) to a less detailed and computationally easier linear ballistic motion model, as explained herein.

As also explained further herein, the transition from the detailed electron transport model and its spiraling trajectory to simplified linear ballistic motion trajectory need not occur exactly at one complete spiraling circumference. In an example, the transition to the more simplified linear ballistic motion trajectory model is assigned a pseudo-random location between one full spiraling circumference and two full spiraling circumferences. This pseudo-random transition can help avoid accumulating a systematic error in radiation dosage over many electrons (some of which may re-enter tissue voxels) due to uniform transitioning between spiraling and linear ballistic models at exactly one complete spiraling circumference, as explained further below.

At 508, for the given electron entering in air, detailed Monte Carlo simulation using a spiraling trajectory model can continue, such as until at least one full spiraling circumference can be completed (or until such other specified cumulative path length threshold has been met).

At 510, for the given electron being simulated using a detailed electron transport model providing spiraling trajectory in the Monte Carlo simulation, if a high density (e.g., tissue voxel) region re-entry is detected, then at 512, the cumulative path length datum corresponding to that electron can be reset to zero, and Monte Carlo simulation using the detailed electron transport model and its spiraling trajectory can continue at 502, for that given electron that has re-entered a high density (e.g., tissue voxel) region. Otherwise, at 510, if the given electron has not re-entered a high density tissue voxel region, then at 514 the cumulative path length datum for the given electron traveling in the air voxel region can be checked to determine whether it exceeds a specified cumulative path length threshold value (e.g., any specified value, such as one full spiraling circumference; one full loop). In an example, this determination can be made a gyroradius of the spiraling trajectory of the detailed electron transport model to determine a loop length corresponding to a full spiraling circumference. At 514, if one full spiraling circumference has not been completed, then at 506, the cumulative path length datum corresponding to the electron can again be incrementally updated (increased) as the detailed electron transport model and its spiraling trajectory is used to simulate an incremental movement of the electron along the spiraling path, such as by continuing at 508 the detailed Monte Carlo simulation using the detailed electron transport model and its spiraling trajectory capability.

At 514, if the cumulative path length datum associated with the given electron traveling in an air voxel region exceeds 1 full loop in the air voxel region without re-entry into a higher density tissue voxel region, then at 518, that electron can be designated for a transition from the more detailed electron transport model to a more simplified linear ballistic motion model in a direction that is aligned with the direction of the applied magnetic field. As mentioned, however, the exact transition from the detailed electron transport model to the simplified linear ballistic model can be deferred to a pseudo-randomly selected location along the spiraling trajectory. This can help avoid a potential systematic error that could otherwise be introduced by simulating all electrons in air voxels as transitioning from a spiraling trajectory to a linear ballistic trajectory after completing exactly one full spiraling circumference. The linear ballistic trajectory model can account for energy loss while traveling through such air voxels, as explained below.

At 520, if a given electron being modeled using a simplified linear ballistic trajectory is detected as re-entering a region of one or more tissue voxels from a region of one or more air voxels, then, at 522, an electron energy datum associated with the given electron can be adjusted for the energy loss due to interactions in air. Such electron energy losses in air can use a more accurate path length in air associated with a spiraling trajectory of a given gyroradius, instead of a more approximate path length in air associated with the linear trajectory. For example, if it is known that a given length on the simplified linear ballistic motion trajectory corresponds to 200 spiraling loops of a given gyroradius if the more detailed electron transport model were used instead, then a cumulative length of such 200 spiraling loops can be used at 522 to determine an energy loss of the electron, even though that electron is being modeled as having a simplified linear ballistic trajectory. Also, at 512, the cumulative path length datum associated with the electron re-entering tissue can be reset to zero, before resuming Monte Carlo simulation of the electron at 502 using the more detailed electron transport model and its spiraling trajectory capability.

A pseudo-randomization of the angle-of entry into the tissue voxels can be employed before resuming the Monte Carlo simulation using the more detailed electron transport model and its spiraling trajectory capability, which can help to avoid introducing systematic error over many electrons transitioning from the more simplified linear ballistic motion model to the more detailed electron transport model with its spiraling trajectory capability. At 520, if the electron being modeled using the simplified linear ballistic trajectory model does not re-enter a tissue voxel region (e.g., exits the simulation volume), then at 524 such electron can be discarded from further simulation for the purpose of determining a radiation dose received by tissue of the subject, such as for radiation treatment planning or administration.

Although the above description with respect to FIG. 5 has emphasized an example in which the voxel data can be segmented into higher density voxels representing tissue and lower density voxels representing air within or outside of the subject, the technique can similarly be applied to other high-density voxels in which a detailed electron transport model allowing for a spiraling electron trajectory capability in an applied magnetic field is useful for providing accuracy, and in which a linear ballistic motion electron trajectory model in an applied magnetic field can be applied with sufficient accuracy to meet a desired objective while reducing the computation complexity of a computer simulation and increasing the simulation speed.

To recap, FIG. 5 describes an example in which photogenerated electrons that have left tissue voxels and entered air voxels can be evaluated to identify electrons that are circling along a spiraling trajectory. The gyroradius of the circumferential spiral trajectory can be modeled based on one or more characteristics, such as an electron energy value that can be stored in an electron energy datum associated with the electron, and a magnetic field strength or direction characteristic of the applied magnetic field, B, at the location of the electron. Thus, even after switching from a detailed electron transport model with spiraling trajectory capability to a less detailed linear ballistic motion model, the actual spiraling distance traversed by the electron in low density air voxels can be determined. By maintaining the detailed electron transport model with its spiraling trajectory capability until at least one full spiral circumference has been traversed, electrons that curve toward and re-enter higher density tissue voxels can be accounted for in radiation treatment dose calculations, while electrons that continue to spiral away into air voxels can be handled in a more computationally efficient manner by applying the linear ballistic trajectory model.

Applying the linear ballistic trajectory model can include the following when transitioning from using the detailed electron transport model with its spiraling trajectory capability. First, a linear estimated direction of the spiraling trajectory can be determined, such as by using an axis through a center of the spiraling trajectory as the linear estimated spiraling direction. Second, this linear estimated direction of the spiraling trajectory can be compared to a direction of the magnetic field B at the location of the electron, such as to determine whether an angle of intersection of the linear estimated direction of the spiraling trajectory is more acute in an angle with the direction of the magnetic field B or is more acute in an angle against the direction of the magnetic field B. Third, the more acute angle can be used to select and assign the direction (with or against the direction of magnetic field) in which the linear ballistic motion trajectory can be projected. Fourth, a linear ballistic motion voxel-to-voxel raytrace can be created in the assigned direction of the linear ballistic motion trajectory, which trajectory can continue so long as the electron continues to remain within a contiguous group of low density voxels, e.g., air voxels. Fifth, upon reaching a high-density voxel (e.g., tissue voxel) an amount of energy associated with losses in air (or other low-density voxel region) can be subtracted from a value stored in the electron energy datum, such as described herein.

In a computer simulation example, a radiation dose modeling Monte Carlo simulation was carried out for 3D imaging voxel data associated with a patient's lower head and neck regions. When electron transport through tissue voxels only were modeled, the simulation time was 152 seconds, in this example. When air voxels were included around the patient, using a detailed electron transport model with a spiraling trajectory to model electron transport through the air voxels, with the added benefit of the accuracy of representing electrons that spiral back into tissue voxels, the simulation time was 585 seconds, in this example. When air voxels were included around the model, using a linear ballistic trajectory model to model electron transport through the air voxels after having completed at least one full spiraling circumference in the air voxels using the detailed electron transport model with its spiraling trajectory, the simulation time was 195 seconds in this example. In sum, the linear ballistic trajectory modeling in the air voxels saved considerable simulation time, which, in turn, can help increase the number of different scenarios that can be feasibly simulated to determine the most appropriate approach to planning and administering radiation treatment to the subject.

Figure 6:
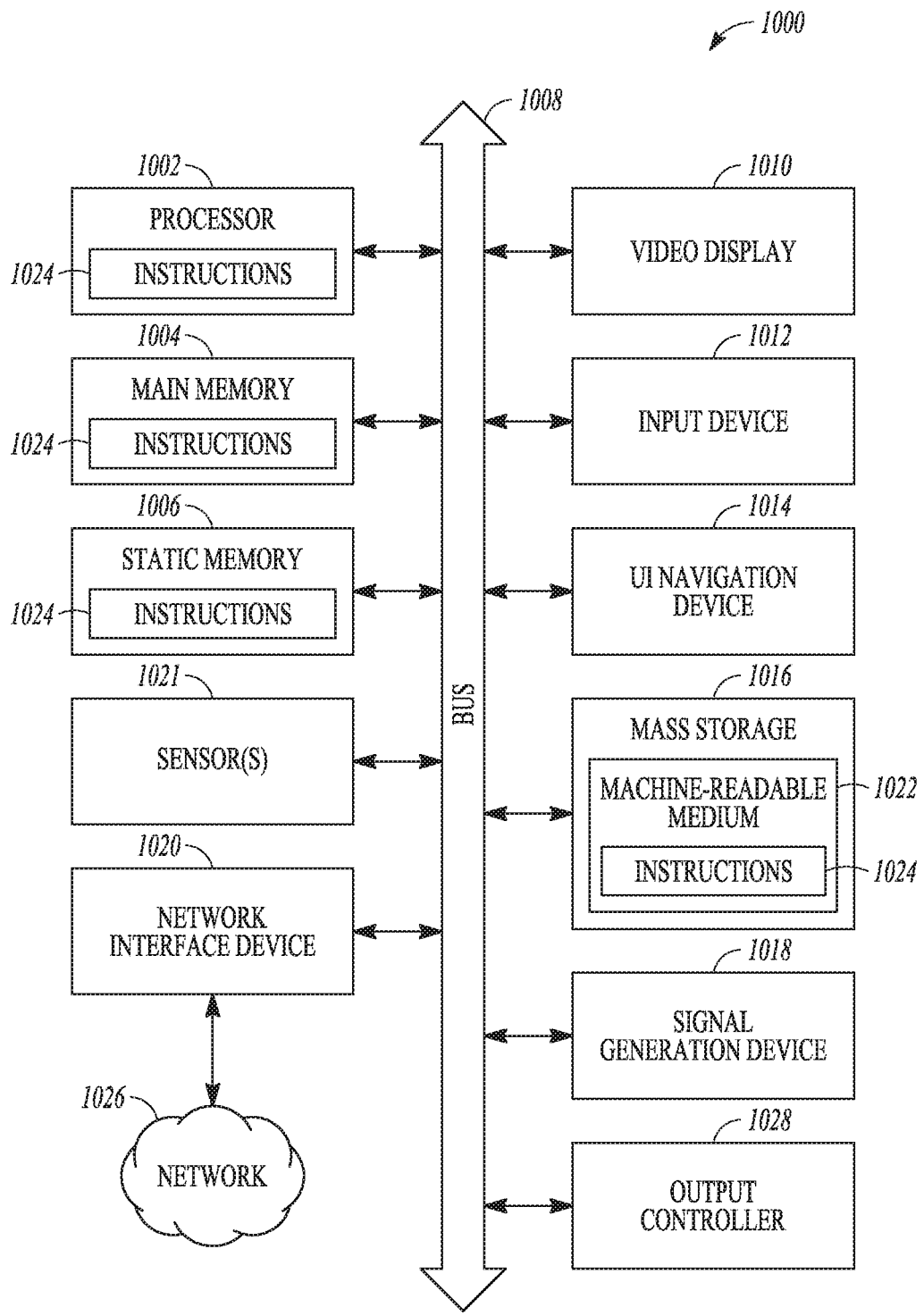
FIG. 6 illustrates a block diagram of an embodiment of a device or machine on which one or more of the methods as discussed herein can be implemented, such as for performing a computer simulation that can include modeling a dose of radiation in a subject, such as where a portion of the subject can be located within an applied magnetic field, such as within the magnetic field produced by a magnetic resonance (MR) imaging device.

FIG. 6 illustrates a block diagram of an embodiment of a device or machine 1000 on which one or more of the methods as discussed herein can be implemented. One or more items of the image processing device 112 can be implemented by the machine 1000. The machine 1000 can operate as a standalone device or may be connected (e.g., networked) to other machines. The image processing device 112 can include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 can include processing circuitry 1002 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. A datum or data associated with the described methods can be stored in or retrieved from such memory, and initialized or updated as desired to carry out the methods described herein. The machine 1000 (e.g., computer system) may further include a video display unit 1010 (e.g., a liquid crystal display (LCD) or a cathode ray tube (CRT)). The machine 1000 can also include an alphanumeric input device 1012 (e.g., a keyboard), a user interface (UI) navigation device 1014 (e.g., a mouse), a disk drive or mass storage unit 1016, a signal generation device 1018 (e.g., a speaker) and a network interface device 1020.

The disk drive unit 1016 can include a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated can include an output controller 1028. The output controller 1028 manages data flow to/from the machine 1000. The output controller 1028 can sometimes be called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device-implemented method of modeling a dose of radiation in a subject in an applied magnetic field, wherein a portion of the modeled dose includes a return electron effect, the modeling including a computer-simulation of electrons leaving and returning to a region due to a modeled Lorentz force induced by the applied magnetic field, the method comprising:
    receiving stored image data including higher density voxels and lower density voxels;
    calculating, using the computer-simulation performed by a computer processor circuit accessing the stored image data, a cumulative path length datum of a computer-simulated electron leaving a higher density voxel and entering a lower density voxel, and setting the cumulative path length datum to zero when the computer-simulated electron returns from a lower density voxel to a higher density voxel; and
    when the cumulative path length datum is determined by the computer processor circuit to exceed a specified path length threshold datum in one or more lower density voxels in the applied magnetic field, modeling a trajectory of the electron in the one or more lower density voxels as linear ballistic motion aligned with the applied magnetic field.

2. The method of claim 1, comprising when the cumulative path length datum does not exceed the specified path length threshold datum in the one or more lower density voxels in the applied magnetic field, modeling the trajectory of the computer-simulated electron using an electron transport model providing a spiraling trajectory induced by the Lorentz force of the applied magnetic field in the one or more lower density voxels.

3. The method of claim 2, comprising using a characteristic of the applied magnetic field to model the spiraling trajectory.

4. The method of claim 3, wherein the characteristic of the applied magnetic field used to model the spiraling trajectory includes at least one of a magnitude or a direction of the applied magnetic field.

5. The method of claim 2, wherein the path length threshold datum is specified to be at least one full spiraling circumference.

6. The method of claim 5, wherein the path length threshold datum is specified to be a position along the spiraling trajectory that is located between one full circumference and two full circumferences.

7. The method of claim 1, comprising using the computer processor circuit for randomly or pseudo-randomly selecting the specified position along the spiraling trajectory that is located beyond a path length value provided by the specified path length threshold datum.

8. The method of claim 1, comprising modeling a computer-simulated electron that has left a higher density voxel to a lower density voxel and then returned to a higher density voxel after being modeled as linear ballistic motion to assign using the computer processor circuit an at least partially randomly or pseudo-randomly specified or other variably specified angle of entry into the higher density voxel.

9. The method of claim 1, further comprising determining, using a Monte Carlo computer simulation performed by the computer processor circuit, a modeled radiation dose within one or more higher density voxels including modeling computer-simulated electrons leaving and returning to a group of one or more higher density voxels.

10. The method of claim 1, wherein the lower density voxels represent a region of air associated with the subject, in which the linear ballistic motion of the modeled trajectory is simulated.

11. The method of claim 10, in which the modeling a trajectory of the computer simulated electron in the one or more lower density voxels as linear ballistic motion aligned with the applied magnetic field includes accounting for an energy loss in the region of air.

12. The method of claim 1, comprising establishing or adjusting a treatment plan of an MR-LINAC or other radiation therapy device based at least in part on the modeled dose of radiation.

13. The method of claim 1, comprising delivering a radiation treatment to the subject directly or indirectly based upon the modeled dose of radiation.

14. A non-transitory device-readable medium including instructions for performing a device-implemented method of modeling a dose of radiation in a subject in an applied magnetic field, wherein a portion of the modeled dose includes modeling that includes a return electron effect including a computer-simulation of electrons leaving and returning to a region due to a modeled Lorentz force induced by the computer simulated applied magnetic field, the method comprising:
    receiving stored image data including higher density voxels and lower density voxels;
    calculating, using the computer-simulation performed by a computer processor circuit accessing the stored image data, a cumulative path length datum of a computer-simulated electron leaving a higher density voxel and entering a lower density voxel, and setting the cumulative path length datum to zero when the computer-simulated electron returns from a lower density voxel to a higher density voxel; and when the cumulative path length datum is determined by the computer processor circuit to exceed a specified path length threshold datum in one or more lower density voxels in the applied magnetic field, modeling a trajectory of the electron in the one or more lower density voxels as linear ballistic motion aligned with the applied magnetic field.

15. The non-transitory device readable medium of claim 14, in which when the cumulative path length datum does not exceed the specified path length threshold datum in the one or more lower density voxels in the applied magnetic field, modeling the trajectory of the computer-simulated electron using an electron transport model providing a spiraling trajectory induced by the Lorentz force of the applied magnetic field in the one or more lower density voxels.

16. A computer system configured for modeling a dose of radiation in a subject in an applied magnetic field, wherein a portion of the modeled dose includes a return electron effect, the modeling including a computer-simulation of electrons leaving and returning to a region due to a modeled Lorentz force by the applied magnetic field, the computer system including a processor circuit configured for:
receiving stored image data including higher density voxels and lower density voxels;
calculating, using the computer-simulation performed by a computer processor circuit accessing the stored image data, a cumulative path length datum of a computer-simulated electron leaving a higher density voxel and entering a lower density voxel, and setting the cumulative path length datum to zero when the computer-simulated electron returns from a lower density voxel to a higher density voxel; and
when the cumulative path length datum is determined by the computer processor circuit to exceed a specified path length threshold datum in one or more lower density voxels in the applied magnetic field, modeling a trajectory of the electron in the one or more lower density voxels as linear ballistic motion aligned with the applied magnetic field.

17. The system of claim 16, wherein the processor circuit is configured for comparing the cumulative path length datum to the specified path length threshold datum, such that when the cumulative path length datum does not exceed the specified path length threshold datum in the one or more lower density voxels in the applied magnetic field, modeling the trajectory of the computer-simulated electron using an electron transport model providing a spiraling trajectory induced by the Lorentz force of the applied magnetic field in the one or more lower density voxels.

18. The system of claim 17, wherein the path length threshold datum is specified to be at least one full spiraling circumference.

19. The system of claim 18, wherein the path length threshold datum is specified to be a position along the spiraling trajectory that is located between one full circumference and two full circumferences.

20. The system of claim 16, wherein the computer processor circuit is configured for randomly or pseudo-randomly selecting the specified position along the spiraling trajectory that is located beyond a path length value provided by the specified path length threshold datum.

21. The system of claim 16, wherein the processor circuit is configured for modeling a computer-simulated electron that has left a higher density voxel to a lower density voxel and then returned to a higher density voxel after being modeled as linear ballistic motion to assign using the computer processor circuit an at least partially randomly or pseudo-randomly specified or other variably specified angle of entry into the higher density voxel.

22. The system of claim 16, included in or coupled to an MR-LINAC or other radiation treatment device for establishing or adjusting a treatment plan based at least in part on the modeled dose of radiation.

* * * * *